United States Patent [19]

Nösberger et al.

[11] Patent Number: 5,276,197
[45] Date of Patent: Jan. 4, 1994

[54] PROCESS FOR MANUFACTURE OF BETA-ISOPHORONE

[75] Inventors: Paul Nösberger, Birsfelden, Switzerland; Adrian J. Vieth, Rümmingen, Fed. Rep. of Germany

[73] Assignee: Hoffman-La Roche Inc., Nutley, N.J.

[21] Appl. No.: 944,027

[22] Filed: Sep. 11, 1992

Related U.S. Application Data

[63] Continuation of Ser. No. 795,409, Nov. 20, 1991, abandoned.

[30] Foreign Application Priority Data

Nov. 30, 1990 [CH] Switzerland ............. 3798/90

[51] Int. Cl.⁵ .............................. C07C 45/67
[52] U.S. Cl. .................................... 568/341
[58] Field of Search .......................... 568/341

[56] References Cited

U.S. PATENT DOCUMENTS

| | | | |
|---|---|---|---|
| 2,246,032 | 6/1941 | Bent | 568/384 |
| 3,397,120 | 8/1968 | Diana et al. | 568/341 |
| 3,670,028 | 6/1972 | Mueller et al. | 568/384 |
| 4,005,145 | 1/1977 | Widmer | 568/341 |
| 4,010,205 | 3/1977 | Becker et al. | 568/341 |
| 4,026,948 | 5/1977 | Becker et al. | 568/341 |
| 4,658,911 | 4/1972 | Pommer et al. | 568/384 |
| 4,845,303 | 4/1989 | Bellut | 568/341 |

FOREIGN PATENT DOCUMENTS

| | | | |
|---|---|---|---|
| 0312735 | 4/1989 | European Pat. Off. | 568/341 |
| 2457157 | 4/1974 | Fed. Rep. of Germany | 568/341 |
| 3421809 | 12/1985 | Fed. Rep. of Germany | 568/384 |
| 52-39655 | 3/1977 | Japan | 568/341 |
| 1-175954 | 7/1989 | Japan | 568/341 |

OTHER PUBLICATIONS

Heymes et al., Synthesis of 3,3,5,5-tetramethyl-4-acetyl-cyclohexanone, Recherches 1971, 18, 106–108.

Chemical Abstracts, vol. 112, No. 15, 1990, Columbus, Ohio, U.S. Abstract No. 138649F, Ito, Nobuhiko, et al.

*Primary Examiner*—James H. Reamer
*Attorney, Agent, or Firm*—George M. Gould; William H. Epstein; Bruce A. Pokras

[57] ABSTRACT

The invention is concerned with a process for the manufacture of beta-isophorone from alpha-isophorone by converting alpha-isophorone into beta-isophorone in the presence of a heterogeneous catalyst in the gas phase. The heterogenous catalyst used is especially an oxide or mixed oxide of the elements Mg, Al, Si and Ni.

7 Claims, No Drawings

PROCESS FOR MANUFACTURE OF BETA-ISOPHORONE

This is a continuation of application Ser. No. 07/795,409 filed Nov. 20, 1991, now abandoned.

The invention relates to a process for the manufacture of beta-isophorone (3,5,5-trimethylcyclohex-3-en-1-one) from alpha-isophorone (3,5,5-trimethylcyclohex-2-en-1-one) by isomerization in the gas phase.

BACKGROUND OF THE INVENTION

Beta-isophorone is of great industrial interest for the synthesis of important classes of compounds. In particular, beta-isophorone is required as an intermediate for ketoisophorone (2,6,6-trimethylcyclohex-2-ene-1,4-dione) which, in turn, is used for the manufacture of vitamin E, various carotinoids, odorants and other natural products.

The manufacture of isophrone takes place by the water-cleaving trimerization of acetone. However, in this case the alpha isomer is the main product formed, in yields above 90%. The thermodynamic equilibrium of the alpha-isophorone/beta-isophorone system lies on the alpha-isophorone side, because by displacing the double bond, a lower energy conjugated system must be converted into a higher energy non-conjugated system. Moreover, the adjustment of this equilibrium takes place slowly. This means that the conversion of alpha-isophorone into beta-isophorone is associated with difficulties.

Of particular interest, therefore, is the isomerization of alpha-isophorone to beta-isophorone in high yield and in an economical manner.

Several processes for the isomerization of alpha-isophorone to beta-isophorone have already been described. The isomerization can be carried out, e.g., by reacting alpha-isophorone with molar amounts of methyl magnesium iodide with the addition of iron(III) chloride, subsequent hydrolysis and distillative working-up [A. Heymes et al., Recherches 1971, 18, 104–108].

The isomerization can also be effected by boiling alpha-isophorone for several hours with triethanolamine, subsequent fractionation and washing the distillate with tartaric acid and sodium chloride solution [DE-OS 2457157].

The catalytic isomerization of alpha-isophorone with acids which dissociate little [U.S. Pat. No. 4,005,145] is a further route to beta-isophorone. In this process the beta-isophorone formed is removed by distillation from the equilibrium. The content of beta-isophorone in the distillation still amounts to 1–2%.

Catalytic isomerization may also be carried out using acetylacetonates or metals of groups IVB, VB, VIB, VIIB and VIIIB of the periodic system as well as aluminium [EP 312 735].

However, all of the known processes have disadvantages, namely:

The adjustment of the equilibrium is a relatively slow process even with the best of the hitherto known catalysts. The weight/time yields are correspondingly low.

A re-isomerization takes place at a reaction temperature above 200° C. in the distillative separation of beta-isophorone from alpha-isophorone. In order to obtain pure beta-isophorone a second distillation under reduced pressure is required.

The energy expenditure for the distillative separation of the alpha-isophorone/beta-isophorone mixture is high, since the content of beta-isophorone is very small.

SUMMARY OF THE INVENTION

A process for the manufacture of beta-isophorone which largely eliminates the disadvantages of the state of the art has now been found. This process comprises isomerizing alpha-isophorone to beta-isophorone in the gas phase in the presence of a heterogeneous catalyst.

DETAILED DESCRIPTION OF THE INVENTION

The object of the invention is a process for the manufacture of beta-isophorone from alpha-isophorone, which process comprises contacting a heated heterogeneous catalyst with gaseous alpha-isophorone to convert the alpha-isophorone into beta-isophorone.

Oxides or mixed oxides, preferably of the elements Mg, Al, Si and Ni, are used as the heterogeneous catalyst. Aluminum silicate can also be used as the catalyst, whereby this should be considered as being a mixed oxide of aluminium and silicon oxides.

The catalyst can be present in pure form, can be mixed with an inert carrier material, especially one which has as little porosity as possible, or can be fixed on an inert, formed carrier material, e.g. ceramic, glass or $\gamma$-aluminum oxide.

Nickel oxide itself or nickel oxide, optionally calcinated, on an inert, formed carrier material (for example ceramic, glass as well as $\gamma$-aluminium oxide) is a preferred catalyst. Nickel oxide on a ceramic carrier material is especially preferred. A further especially preferred catalyst is nickel oxide, calcinated at a temperature of $\geq 1000°$ C., on a $\gamma$-aluminium oxide carrier.

The catalyst preferably has a specific surface of about 1–50 m$^2$/g and an amount of micropores and small mesopores which is as low as possible.

The process in accordance with the invention can be carried out preferably in a solid bed reactor.

Dilution with an inert gas is possible, but is not essential for the performance of the isomerization reaction. The pressure under which the reaction is carried out is not critical. Preferably, the reaction is carried out at a pressure of about 1 kPa to about 200 kPa. In an especially preferred embodiment, the reaction is carried out at atmospheric pressure.

The time period during which the alpha-isophorone is in contact with the catalyst is not critical. In general, the contact time of the alpha-isophorone with the catalyst should lie in the range of about 0.1 second to about 10 seconds, with the range of about 0.5 second to about 2 seconds being preferred. The throughput of alpha-isophorone conveniently amounts to 1–10 kg/h·l. In other words, 1–10 kg of alpha-isophorone are suitably used per liter of catalyst and hour.

The reaction conditions may be optimized by charging the catalyst and, if desired, inert carrier material into the reactor (preferably a solid bed reactor) and then adjusting the contact time and the temperature so that the conversion of alpha-isophorone to beta-isophorone is optimal and no byproducts are formed.

The temperature at which the reaction is carried out is not critical so long as it is sufficient to cause of conversion of alpha-isophorone into beta-isophorone and is below the decomposition temperature of both compounds. The reaction is preferably carried out in a temperature range of about 300° C. to 450° C.

Gaseous alpha-isophorone, optionally diluted with an inert gas, is conveniently conducted through the heated reaction zone filled with the catalyst which is undiluted or which is fixed on an inert carrier material or mixed therewith. Depending on the reaction temperature, the reaction products contain 5–11% of beta-isophorone and 89–95% of alpha-isophorone. Byproducts, for example gamma-isophorone (3-methylene-5,5-dimethyl-cyclohexan-1-one), hydrocarbons, 3,5-xylenol and 2,3,5-trimethylphenol, are formed only in insignificant amounts. The reaction products are separated by any conventional means, for example by distillation. Especially preferred is the direct introduction of the reaction products into a continuously operating rectification column, whereby beta-isophorone with a content of about 97% accrues at the head. The product at the bottom of the column can be returned to the reactor without further purification.

EXAMPLE 1

Nickel oxide (Merck 6723) having a granulation of 1–3 mm is used as the catalyst. 1% Luviskol K90 (polyvinylpyrrolidone) is added for the granulation of the nickel oxide powder. 45 ml of this catalyst are filled into an electrically heated glass tube having a diameter of 2.4 cm. The glass tube is filled with glass wool to a height of about 4 cm above the catalyst. 18 ml of alpha-isophorone and 1.8 l of nitrogen per hour are then introduced from above at a temperature of 300° C. The reaction products contain 9% of beta-isophorone and 91% of alpha-isophorone.

EXAMPLE 2

Commerically available nickel oxide (Strem 28-148; 15% nickel oxide on γ-aluminium oxide) is used as the catalyst. This is calcinated at 1200° C. for 3 hours prior to use. The apparatus in which the isomerization is carried out consists of an externally heatable evaporation flask having situated above it a reaction tube heated electrically from the outside. A feed pipe leads to a condenser which is attached to a receiver. The isomerization reaction is carried out at a pressure of 2 kPa.

45 ml of glass beads and then 100 ml of catalyst are firstly filled into the reaction tube (diameter 5 cm). The temperature of the catalyst is adjusted to 300° C. The evaporation flask is heated to 105° C. About 100 ml of reaction product having a beta-isophorone content of 6–7% are removed each hour. The mixture also contains about 93% of alpha-isophorone and about 0.3% of γ-isophorone.

EXAMPLE 3

30 ml of a magnesium oxide catalyst (Mg-0601T from Harshaw) are filled into an electrically heated glass tube (diameter 2 cm). Ceramic beads are situated above and below. 4 l nitrogen per hour and 90 ml of alpha-isophorone per hour are introduced at a reaction temperature of 300° C. The reaction products consist of 7.6% of beta-isophorone, 91.8% of alpha-isophorone and 0.6% of byproducts.

EXAMPLE 4

Alpha-aluminium oxide (A 980 from Rosenthal) is used in place of the magnesium oxide catalyst from Example 3. The reaction is carried out analogously to Example 3. The reaction mixture contains 6.8% of beta-isophorone. No byproducts can be detected.

EXAMPLE 5

Silicon dioxide having a specific surface of 50 m²/g (Shell S980G/2.5) is used as the catalyst. The reactor consists of an electrically heated steel tube (heating zone: 43 cm; diameter 2.7 cm). 40 ml of catalyst are introduced. The reactor is filled in the lower and upper parts with ceramic beads (diameter 0.6 cm). Between 60 and 240 ml of alpha-isophorone per hour are introduced into the reactor at a reaction temperature of 300° C. The reaction mixture contains, independently of the amount of isophorone introduced, 5.5% of beta-isophorone and 94.5% of alpha-isophorone.

EXAMPLE 6

Aluminium silicate (Norton SA-3232) having a specific surface of 30 m²/g is used as the catalyst. The same reactor and the same amount of catalyst as in Example 5 are used. 4 l of nitrogen and 180 ml of alpha-isophorone are introduced into the reactor hourly.

The yield of beta-isophorone depends on the reaction temperature and is illustrated in the following Table.

TABLE

Dependence of beta-isophorone content on reaction temperature

| Temperature °C. | β-Isophorone % | α-Isophorone % | Byproducts % |
|---|---|---|---|
| 300 | 5.0 | 95.0 | — |
| 350 | 6.8 | 93.2 | — |
| 400 | 9.2 | 90.8 | — |
| 450 | 11.3 | 84.7 | 4.0ᵃ⁾ |

ᵃ⁾The amount of byprducts formed can be reduced by increasing the isophorone input.

EXAMPLE 7

The same catalyst and the same reactor as in Example 6 are used. 100 ml of catalyst are used. The reaction temperature is adjusted to 350° C. and 400 g of alpha-isophorone are introduced into the reactor hourly. The reaction has finished after 40 hours. The reaction product contains 7.7% of beta-isophorone. No byproducts can be detected. The activity of the catalyst remains constant during the period of the experiment.

We claim:

1. A process for the manufacture of beta-isophorone from alpha-isophorone comprising contacting a heterogeneous catalyst which has been heated to a temperature from about 300° C. to about 450° C. with gaseous isophorone to convert alpha-isophorone into beta-isophorone, said catalyst comprising an oxide or mixed oxides of elements selected from the group consisting of Mg, Al, Si and Ni.

2. A process according to claim 1 wherein the catalyst is heated to a temperature from about 300° C. to about 450° C.

3. A process according to claim 2 wherein the contact occurs for a period of about 0.1 seconds to about 10 seconds.

4. A process according to claim 3 wherein the catalyst has a specific surface of 1–50 m²/g.

5. A process according to claim 4, wherein the catalyst is aluminium oxide, silicone oxide or aluminium silicate.

6. A process according to claim 4 wherein nickel oxide on a ceramic carrier material is used as the catalyst.

7. A process according to claim 4 wherein nickel oxide, calcinated at a temperature of ≧1000° C., on a γ-aluminium oxide carrier is used as the catalyst.

* * * * *